(12) United States Patent
Coneski et al.

(10) Patent No.: US 9,139,684 B2
(45) Date of Patent: Sep. 22, 2015

(54) CARBOXYBETAINE-FUNCTIONALIZED DIOLS AND ZWITTERIONIC POLYURETHANE HYDROGELS DERIVED THEREFROM

(71) Applicants: Peter N. Coneski, Alexandria, VA (US); James H Wynne, Alexandria, VA (US)

(72) Inventors: Peter N. Coneski, Alexandria, VA (US); James H Wynne, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 155 days.

(21) Appl. No.: 13/783,481

(22) Filed: Mar. 4, 2013

(65) Prior Publication Data

US 2014/0024768 A1  Jan. 23, 2014

Related U.S. Application Data

(60) Provisional application No. 61/673,892, filed on Jul. 20, 2012.

(51) Int. Cl.
| | |
|---|---|
| *C08G 18/32* | (2006.01) |
| *C08G 18/38* | (2006.01) |
| *C08G 18/73* | (2006.01) |
| *C08G 18/78* | (2006.01) |
| *C08G 18/79* | (2006.01) |
| *C08G 18/82* | (2006.01) |
| *C07C 229/12* | (2006.01) |
| *C07C 227/10* | (2006.01) |
| *C08G 18/08* | (2006.01) |
| *C07C 227/02* | (2006.01) |

(52) U.S. Cl.
CPC .......... *C08G 18/3821* (2013.01); *C07C 227/02* (2013.01); *C07C 227/10* (2013.01); *C07C 229/12* (2013.01); *C08G 18/0833* (2013.01); *C08G 18/3206* (2013.01); *C08G 18/381* (2013.01); *C08G 18/3804* (2013.01); *C08G 18/73* (2013.01); *C08G 18/7831* (2013.01); *C08G 18/791* (2013.01); *C08G 18/792* (2013.01); *C08G 18/82* (2013.01); *C08G 2210/00* (2013.01)

(58) Field of Classification Search
USPC ...................................................... 528/70, 71
IPC ........ C08G 18/0833,18/3206, 18/3804, 18/381, C08G 18/3821, 18/73, 18/7831, 18/791, 18/792, C08G 18/82, 2210/00
See application file for complete search history.

(56) References Cited

FOREIGN PATENT DOCUMENTS

WO    2011/057219 A2    5/2011

OTHER PUBLICATIONS

Carr et al., "Functionalizable and nonfouling zwitterionic carboxybetaine hydrogels with a carboxybetaine dimethacrylate crosslinker" Biomaterials 32 (2011) 961-968.
Carr et al., "Uniform zwitterionic polymer hydrogels with a nonfouling and functionalizable crosslinker using photopolymerization" Biomaterials 32 (2011) 6893-6899.
Coneski et al., "Zwitterionic Polyurethane Hydrogels Derived from Carboxybetaine-Functionalized Diols" ACS Appl. Mater. Interfaces 2012, 4, 4465?4469.
Kabiri et al., "Novel sulfobetaine-sulfonic acid-contained superswelling hydrogels" Polym. Adv. Technol. 2005; 16: 659-666.

*Primary Examiner* — Rabon Sergent
(74) *Attorney, Agent, or Firm* — US Naval Research Laboratory; Joseph T. Grunkemeyer (57) ABSTRACT

A compound having the formula: $X^-N^+(CH_3)(CH_2CH_2OH)_2[(CH_2)_n-COO-R^1]$ and a polymer having the repeat unit: $X^-\{-OCH_2CH_2-N^+(CH_3)[(CH_2)_n-CO-Y]-CH_2CH_2O-CO-NH-R^2-NH-CO-\}$. $R^1$ is an ester protecting group, $R^2$ is an organic group, X is a halide, and n is a positive integer. Each Y is $O^-Z^+$ or $O-R^1$, where $Z^+$ is a cation from an aqueous base. A method of reacting N-methyldiethanolamine with an ω-halo-n-alkanoate ester to form the above compound.

21 Claims, 5 Drawing Sheets

CARBOXYBETAINE-FUNCTIONALIZED DIOLS AND ZWITTERIONIC POLYURETHANE HYDROGELS DERIVED THEREFROM

This application claims the benefit of U.S. Provisional Application No. 61/673,892, filed on Jul. 20, 2012. The provisional application and all other publications and patent documents referred to throughout this nonprovisional application are incorporated herein by reference.

TECHNICAL FIELD

The present disclosure is generally related to zwitterionic hydrogels.

DESCRIPTION OF RELATED ART

Nonspecific adsorption of proteins and cells onto surfaces continues to be an unresolved problem that is particularly detrimental in medical, industrial, and marine applications (Hori et al., "Bacterial adhesion: From mechanism to control" *Biochemical Engineering Journal* 2010, 48 (3), 424-434). Bacterial adhesion specifically has been shown to result in the formation of biofilms that lead to devastating results across applications. For example, biofilm formation on medical implants results in the formation of persistent infections that are up to 1000 times more resistant to conventional antibiotics than free bacteria (Costerton et al., "Bacterial Biofilms: A Common Cause of Persistent Infections" *Science* 1999, 284 (5418), 1318-1322; Drenkard, "Antimicrobial resistance of Pseudomonas aeruginosa biofilms" *Microbes and Infection* 2003, 5 (13), 1213-1219). In a similar manner, marine biofilms have been shown to condition underwater structures for the settlement of a variety of marine species ranging from barnacles and mussels to algae and tubeworms (Callow et al., "Marine Biofouling: A Sticky Problem" *Biologist* 2002, 49 (1)). The adhesion of these organisms collectively results in increased vessel drag, reducing operational speeds and increasing both fuel consumption and maintenance costs (Abbott et al., "Cost-benefit analysis of the use of TBT: the case for a treatment approach" *Science of The Total Environment* 2000, 258 (1-2), 5-19; Champ, "A review of organotin regulatory strategies, pending actions, related costs and benefits" *Science of The Total Environment* 2000, 258 (1-2), 21-71; Cooney et al., [47] Quantifying effects of antifouling paints on microbial biofilm formation. In *Methods in Enzymology*, Ron, J. D., Ed. Academic Press: 1999; Vol. Volume 310, pp 637-644; Rouhi, "The Squeeze On Tributyltins" *Chemical & Engineering News Archive* 1998, 76 (17), 41-42; Yebra et al., "Antifouling technology-past, present and future steps towards efficient and environmentally friendly antifouling coatings" *Progress in Organic Coatings* 2004, 50 (2), 75-104).

Passive strategies to minimize the initial colonization of these fouling species onto surfaces have utilized surface modifications that traditionally impart either low surface energies or high degrees of hydration. For example, low surface energy silicones (Kim et al., "Adhesion study of silicone coatings: the interaction of thickness, modulus and shear rate on adhesion force" *Biofouling* 2007, 23 (2), 113-120; Sommer et al., "A preliminary study on the properties and fouling-release performance of siloxane-polyurethane coatings prepared from poly(dimethylsiloxane) (PDMS) macromers" *Biofouling* 2010, 26 (8), 961-972; Majumdar et al., "Combinatorial Materials Research Applied to the Development of New Surface Coatings XV: An Investigation of Polysiloxane Anti-Fouling/Fouling-Release Coatings Containing Tethered Quaternary Ammonium Salt Groups" *ACS Combinatorial Science* 2011, 13 (3), 298-309) and fluoropolymers (Gudipati et al., "The Antifouling and Fouling-Release Performance of Hyperbranched Fluoropolymer (HBFP)-Poly(ethylene glycol) (PEG) Composite Coatings Evaluated by Adsorption of Biomacromolecules and the Green Fouling Alga Ulva" *Langmuir* 2005, 21 (7), 3044-3053; Hu et al., "Photochemically Cross-Linked Perfluoropolyether-Based Elastomers: Synthesis, Physical Characterization, and Biofouling Evaluation" *Macromolecules* 2009, 42 (18), 6999-7007; Wang et al., "Photocurable Amphiphilic Perfluoropolyether/Poly(ethylene glycol) Networks for Fouling-Release Coatings" *Macromolecules* 2011, 44 (4), 878-885) have been implicated as promising antifouling materials as was previously predicted by the Baier curve (Baier et al., "Role of an artificial boundary in modifying blood proteins" *Federation proceedings* 1971, 30 (5), 1523-38). Conversely, the high hydration capacities of poly(ethylene glycol) (PEG) (Boozer et al., "Surface functionalization for self-referencing surface plasmon resonance (SPR) biosensors by multi-step self-assembly" *Sensors and Actuators B: Chemical* 2003, 90 (1-3), 22-30; Langer, "Drugs on Target" *Science* 2001, 293 (5527), 58-59; Prime et al., "Self-assembled organic monolayers: model systems for studying adsorption of proteins at surfaces" *Science* 1991, 252 (5009), 1164-1167) and zwitterionic materials (Chen et al., "An New Avenue to Nonfouling Materials" *Advanced Materials* 2008, 20 (2), 335-338; Cheng et al., "Zwitterionic carboxybetaine polymer surfaces and their resistance to long-term biofilm formation" *Biomaterials* 2009, 30 (28), 5234-5240; Zhang et al., "Polysulfobetaine-Grafted Surfaces as Environmentally Benign Ultralow Fouling Marine Coatings" *Langmuir* 2009, 25 (23), 13516-13521) have also shown excellent antifouling character. Zwitterionic hydrogels are particularly suited as antifouling materials due to their ultra-low-fouling characteristics (less than 5 ng/cm$^2$ protein adsorption) (Yang et al., "Pursuing 'Zero' Protein Adsorption of Poly(carboxybetaine) from Undiluted Blood Serum and Plasma" *Langmuir* 2009, 25 (19), 11911-11916; Yang et al., "Functionalizable and ultra stable nanoparticles coated with zwitterionic poly(carboxybetaine) in undiluted blood serum" *Biomaterials* 2009, 30 (29), 5617-5621) arising from the high hydration capacities surrounding the opposing charges of the material (He et al., "Molecular Simulation Studies of Protein Interactions with Zwitterionic Phosphorylcholine Self-Assembled Monolayers in the Presence of Water" *Langmuir* 2008, 24 (18), 10358-10364). In addition, there is less susceptibility for oxidative damage to zwitterionic material than there is for PEG-based hydrogels (Herold et al., "Oxidation of polyethylene glycols by alcohol dehydrogenase" *Biochemical Pharmacology* 1989, 38 (1), 73-76; Ostuni et al., "A Survey of Structure-Property Relationships of Surfaces that Resist the Adsorption of Protein" *Langmuir* 2001,17 (18), 5605-5620). Despite this, the lack of mechanical integrity of hydrogels in general continues to be a hindrance for their implementation in many potential applications (Huglin et al., "Influence of temperature on swelling and mechanical properties of a sulphobetaine hydrogel" *Polymer* 1991, 32 (18), 3354-3358).

BRIEF SUMMARY

Disclosed herein is a compound having the formula:
$X^-N^+(CH_3)(CH_2CH_2OH)_2[(CH_2)_n-COO-R^1]$. $R^1$ is an ester protecting group, X is a halide, and n is a positive integer.

Also disclosed herein is a polymer comprising the repeat unit:
X⁻{—OCH₂CH₂—N⁺(CH₃)[(CH₂)ₙ—CO—Y]—CH₂CH₂O—CO—NH—R²—NH—CO—}. R¹, X, and n are as defined above. R² is an organic group. Each Y is independently selected from O⁻Z⁺ and O—R¹. Z⁺ is a cation from an aqueous base.

Also disclosed herein is a method comprising: reacting N-methyldiethanolamine with an ω-halo-n-alkanoate ester to form a compound having the formula: X⁻N⁺(CH₃)(CH₂CH₂OH)₂[(CH₂)ₙ—COO—R¹]. R¹, X, and n are as defined above.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is the synthesis of novel zwitterionic polyurethane hydrogels with tunable water uptake via the polymerization of protected carboxybetaine-functionalized diols with polyisocyanates. Post-polymerization hydrolysis of monomeric side chain ethyl esters establishes zwitterionic carboxybetaine functionalities that facilitate water uptake via the enhanced hydration capacities surrounding the opposing charges of the diol component. Tunable hydration of these materials, ranging from 24-250% solution uptake based on the dry polymer weight, may be achieved by controlling structural characteristics of the diol precursor, such as ammonium/carboxylate spacing and ethyl ester hydrolysis conditions (i.e. exposure time to aqueous base).

One of the main problems associated with the implementation of hydrogels is the lack of mechanical integrity upon hydration. To combat this a hydrogel is disclosed with tunable solution uptake based on the extent of deprotection of a carboxybetaine moiety polymerized into the matrix. As ester deprotection in the bulk material is likely limited by diffusion, the potential exists to limit deprotection at or near the surface of these materials creating a material that behaves as a hydrogel at the material interface, but not in the bulk. Prevention of this water uptake in the bulk of the material may provide enhanced mechanical stability compared to matrices that are fully hydrated throughout the bulk material.

The successful synthesis of zwitterionic polyurethanes hydrogels derived from protected carboxybetaine diols has been demonstrated. The degree of water uptake of these polymers was found to be influenced by both the carboxybetaine structure and deprotection time. Diffusion-controlled deprotection of the carboxybetaine moiety allows for the preparation of gradient hydrogels with the depth and overall amount of hydration dependent on deprotection time. The hydrogels may be useful as antifouling materials.

Figure 1:
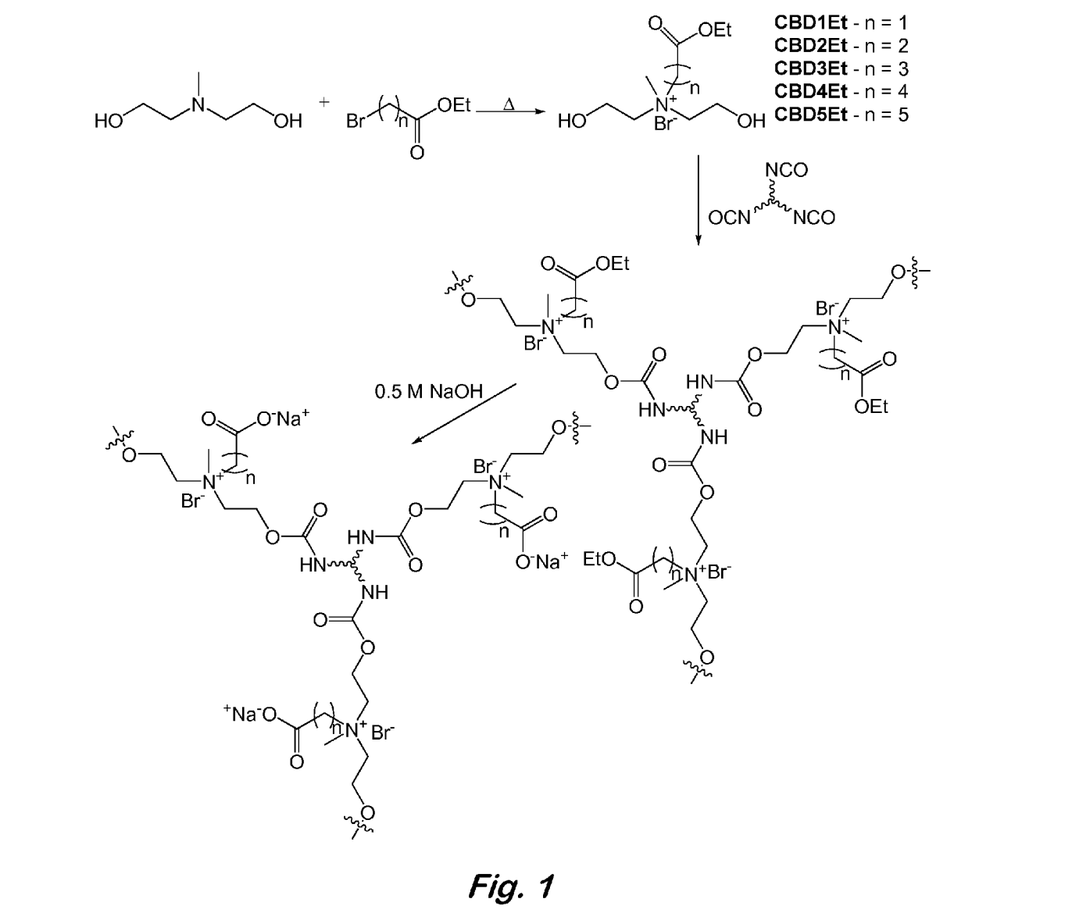
FIG. 1 shows the synthesis scheme of ethyl ester protected carboxybetaine diols, subsequent polymerization with polyisocyanate, and ester deprotection to generate zwitterionic polyurethane hydrogels.

In the first step of the synthesis method (FIG. 1), N-methyldiethanolamine (HO—CH₂CH₂—N(CH₃)—CH₂CH₂—OH) is reacted with an ω-halo-n-alkanoate ester. Such esters have the formula X—(CH₂)ₙ—COO—R¹, where X is a halogen such as bromium. The value n may be any positive integer including, but not limited to, 1, 2, 3, 4, 5, and integers up to 10 or 100. The R¹ group may be an ester protecting group including, but not limited to, methyl, ethyl, alkyl, silyl, or any other protecting group known in the art that can be removed by a base. The reaction may be performed by any method of using an alkyl halide to alkylate an amine. The two reactants may be heated in a neat mixture or in a solvent without the need of a catalyst. The reaction forms a compound having the formula X⁻N⁺(CH₃)(CH₂CH₂OH)₂[(CH₂)ₙ—COO—R¹].

In an alternative reaction scheme, an ω-amino-n-alkanoic acid is reacted with two moles of 2-bromoethanol to form an N,N-bis(2-hydroxyethyl)-ω-amino-n-alkanoic acid. Reacting this compound with ethanol produces an ethyl-N,N-bis(2-hydroxylethyl)-ω-amino-n-alkanoate. Other hydroxyl forms of ester protecting groups may be used as well as ethanol. Finally, reaction with bromomethane results in the Br⁻N⁺(CH₃)(CH₂CH₂OH)₂[(CH₂)ₙ—COO—R¹] compound. Methods of performing the individual reaction steps and alternatives thereof are known in the art. This method may be suitable where n is 2.

In the next step, the compound is reacted with a polyisocyanate (OCN—R²—NCO), whereby the isocyanate groups and hydroxyl groups form urethane linkages. The reaction may be performed by any method for making polyurethanes. Such reactions generally occur spontaneously, though they may be catalyzed if necessary. Dimethylformamide is a suitable solvent. Dimethylsulfoxide may also be used as a solvent, and may be suitable where n is 1, but nearly complete removal of this high boiling solvent may be needed for subsequently forming a hydrogel. The reaction forms a polymer comprising the repeat unit X⁻{—OCH₂CH₂—N⁺(CH₃)[(CH₂)ₙ—COO—R¹]—CH₂CH₂O—CO—NH—R²—NH—CO—}.

Any polyisocyanate where the R² group is an organic group may be used. Suitable polyisocyanates include, but are not limited to, aliphatic polyisocyanates such as hexamethylene diisocyanate and biurets and trimers thereof Polyisocyanates having an isocyanate functionality greater than 2 may be used to form a crosslinked structure.

In the next step, a hydrogel comprising the polymer is made by allowing a sample of the polymer to absorb water. Any amount of water that can be absorbed by the polymer may be used. As part of this step or as a subsequent step, the hydrogel or an article comprising the polymer is exposed to an aqueous base. The exposure may have two effects: 1) conversion of a portion of the ester protecting groups to carboxylate groups, which may facilitate 2) increased uptake of water into the hydrogel. After the exposure, the polymer has the formula X-{—$^{OCH}$$_2$CH$_2$—N$^+$(CH$_3$)[(CH$_2$)$_n$—CO—Y]—CH$_2$CH$_2$O—CO—NH—R$^2$—NH—CO—}. Each Y may be O$^-$Z$^+$ or O—R$^1$, where Z$^+$ is the cation from the base. NaOH is one suitable base, and any concentration of the base that produces at least some carboxylate groups with causing overall degradation of the hydrogel may be used. As the base may not necessarily penetrate throughout the article or hydrogel, it may have a gradient in the concentration of O$^-$Z$^+$ groups. For example, there may be a greater concentration of O$^-$Z$^+$ groups near the surface of the hydrogel than in the interior.

By way of example, the diol precursors were synthesized neat or in N,N-dimethylformamide (DMF) by heating 1.0 equiv N-methyldiethanolamine (MDEA) with 1.0 equiv of a brominated ethyl ester at 60° C. for 24 h with magnetic stirring. In detail, N-methyldiethanolamine was heated at 60° C. in a 100 mL round bottom flask with an equimolar amount of a brominated ethyl ester (ethyl bromoacetate, ethyl 3-bromopropionate, ethyl 4-bromobutyrate, ethyl 5-bromovalerate, or ethyl 6-bromohexanoate) and magnetically stirred. In the case of reactions containing ethyl bromoacetate or ethyl 3-bromopropionate, 10 mL of N,N'-dimethylformamide (DMF) was also added to the reaction. After 24 h, the reaction was removed from heat and quickly transferred from the round bottom flask to a vial. Diol CBD1Et precipitated from the DMF solution as a white solid and was vacuum filtered and washed with acetone (since it was only soluble in protic solvents it was not used further). CBD3Et solidified upon cooling and was used without further purification. CBD4Et and CBD5Et remained viscous transparent oils and were also used without further purification.

The protected carboxybetaine diol, CBD2Et, could not be synthesized via this method. The acidic nature of the α-proton adjacent to the carbonyl of ethyl 3-bromopropionate promoted elimination of the proximal bromine atom upon reaction with MDEA, resulting in high yields of an alkene byproduct. However, all other intended diol species were isolated in high yield as either white solids (CBD1Et and CBD3Et) or clear oils (CBD4Et and CBD5Et), with their structures confirmed by $^1$H and $^{13}$C NMR as follows.

CBD3Et: $^1$H NMR (DMSO-d$_6$, δ): 5.28-5.25; (t, 2H), 4.12-4.05; (m, 2H), 3.84; (m, 4H), 3.53-3.49; (m,4H), 3.46-3.43; (m, 2H), 3.15; (s, 3H), 2.41-2.37; (t, 2H), 1.96; (m, 2H), 1.23-1.18; (t, 3H). $^{13}$C NMR (DMSO-d$_6$, δ): 171.8, 63.2, 61.0, 60.1, 54.6, 49.2, 30.1, 17.5, 14.0.

CBD4Et: $^1$H NMR (DMSO-d$_6$, δ): 5.27-5.23; (t, 2H), 4.10-4.03; (m, 2H), 3.85-3.83; (m, 4H), 3.52-3.50; (m, 4H), 3.44; (m, 2H), 3.15; (s, 3H), 2.40-2.35; (t, 2H), 1.76; (m, 2H), 1.56-1.53; (m, 2H), 1.21-1.17; (t, 3H). $^{13}$C NMR (DMSO-d$_6$, δ): 172.4, 63.1, 61.8, 59.7, 54.6, 49.0, 32.7, 21.2, 21.0, 14.0.

CBD5Et: $^1$H NMR (DMSO-d$_6$, δ): 5.26-5.23; (t, 2H), 4.09-4.02; (m, 2H), 3.86-3.83; (m, 4H), 3.54-3.52; (m, 4H), 3.47-3.42; (m, 2H), 3.16; (s, 3H), 2.34-2.29; (t, 2H), 1.73 (m, 2H), 1.60-1.55; (m, 2H), 1.30-1.28; (m, 2H), 1.21-1.16; (t, 3H). $^{13}$C NMR (DMSO-d$_6$, δ): 172.7, 63.0, 62.2, 59.6, 54.6, 49.0, 33.1, 25.1, 23.8, 21.3, 14.1.

In order to facilitate mixing of the polymer components and initiate cross-linking, polyisocyanate (DESMODUR® N 3600 polyisocyanate, Bayer MaterialScience, 1.0 equiv NCO) and diol (1.0 equiv OH) were mixed with a small amount of DMF and magnetically stirred in a round bottom flask at 60° C. for 30 min. The viscous solution was then solution cast or poured into a mold and cured at 80° C. for 24 hr. However, the extremely high melting point and insolubility of CBD1Et in any aprotic solvents prevented its polymerization into a polyurethane matrix. Cured polyurethanes were colorless to light yellow, optically transparent, and flexible. Control materials were also synthesized via the same procedure using ethylene glycol (EG), diethylene glycol (DEG), triethylene glycol (TEG), and PEG as alternative diols.

Figure 2:
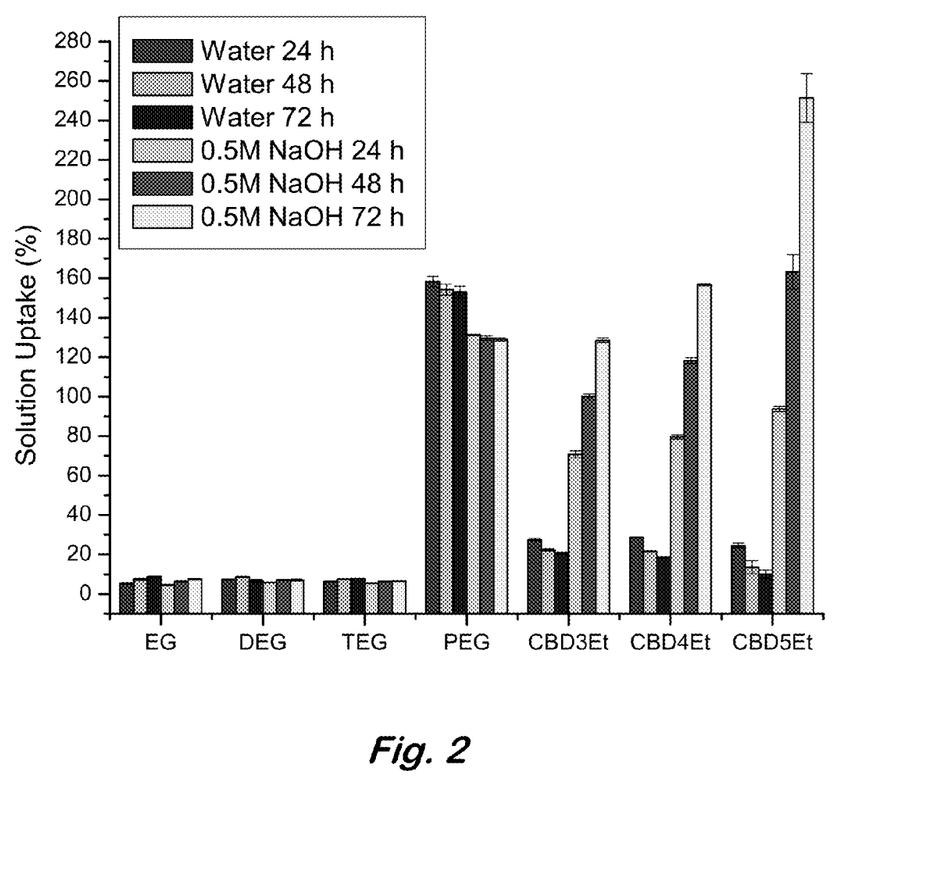
FIG. 2 shows solution uptake of carboxybetaine and control polyurethanes as a function of diol structure and solution composition.

Cured polyurethanes (test ex. Polydesmo CBD3Et; control ex. Polydesmo EG, etc) were subjected to a variety of characterization techniques including gel fraction analysis, water uptake, TGA, DSC, DMA and IR to determine their utility as hydrogels. As was expected based on the presence of ethyl esters protecting the carboxylate functionalities, the untreated test polyurethanes exhibited low water uptake compared to the PEG-based polyurethane hydrogel (ca. 25-29% vs. 158%). However, upon exposure to weak aqueous base, the solution uptake and swelling properties of the polyurethanes increased drastically (FIG. 2). Base induced ester hydrolysis cleaved the protecting group restoring the carboxylate anion, thereby completing the carboxybetaine moiety and increasing the hydration capacities of the functionalized networks to between 74 and 91% of the dry polymer weight after 24 hr exposure to 0.5 M NaOH. Additional exposure to aqueous base enhanced water uptake further with total water uptake values increasing to between 129-251% of the dry polymer weight after 3 days of base exposure. Total water uptake was not only determined to be a function of deprotection time, but also the structure of the carboxybetaine moiety. Although increasing the carbon spacing between the ammonium and carboxylate ions from 3 to 5 carbons only enhanced solution uptake by 31% after 1 day of hydrolysis this value increased with increasing time up to 96% after a 3 day deprotection soak. Overall, incorporation of CBD5 imparted approximately 30% additional solution uptake per day exposed to NaOH compared to CBD3, and 20% per day compared to CBD4. This is attributed to the greater spatial distribution of charge in the larger carboxybetaine moiety, which allows for elevated hydration capacity. Furthermore, the consistent increase in solution uptake daily indicates that the rate of deprotection is not significantly influenced by these structural changes of the carboxybetaine moiety and is more likely a factor of the protecting group, which in this case is common among all derivatives. Importantly, exposure of control materials to aqueous base showed no increase in solution uptake compared to water, and no additional uptake beyond the first time point was observed. Additionally, no unintended degradation of the polymer matrix was noted during the exposure to low concentrations of aqueous base. Furthermore, as no significant increase in solution uptake was noted for test materials even after 4 weeks of soak time in water, sufficient deprotection of the ethyl ester group does not seem to occur at neutral pHs. This indicates that the overall water uptake of these materials may be controlled based on treatment time with a deprotection solution post-polymerization.

Figure 3:
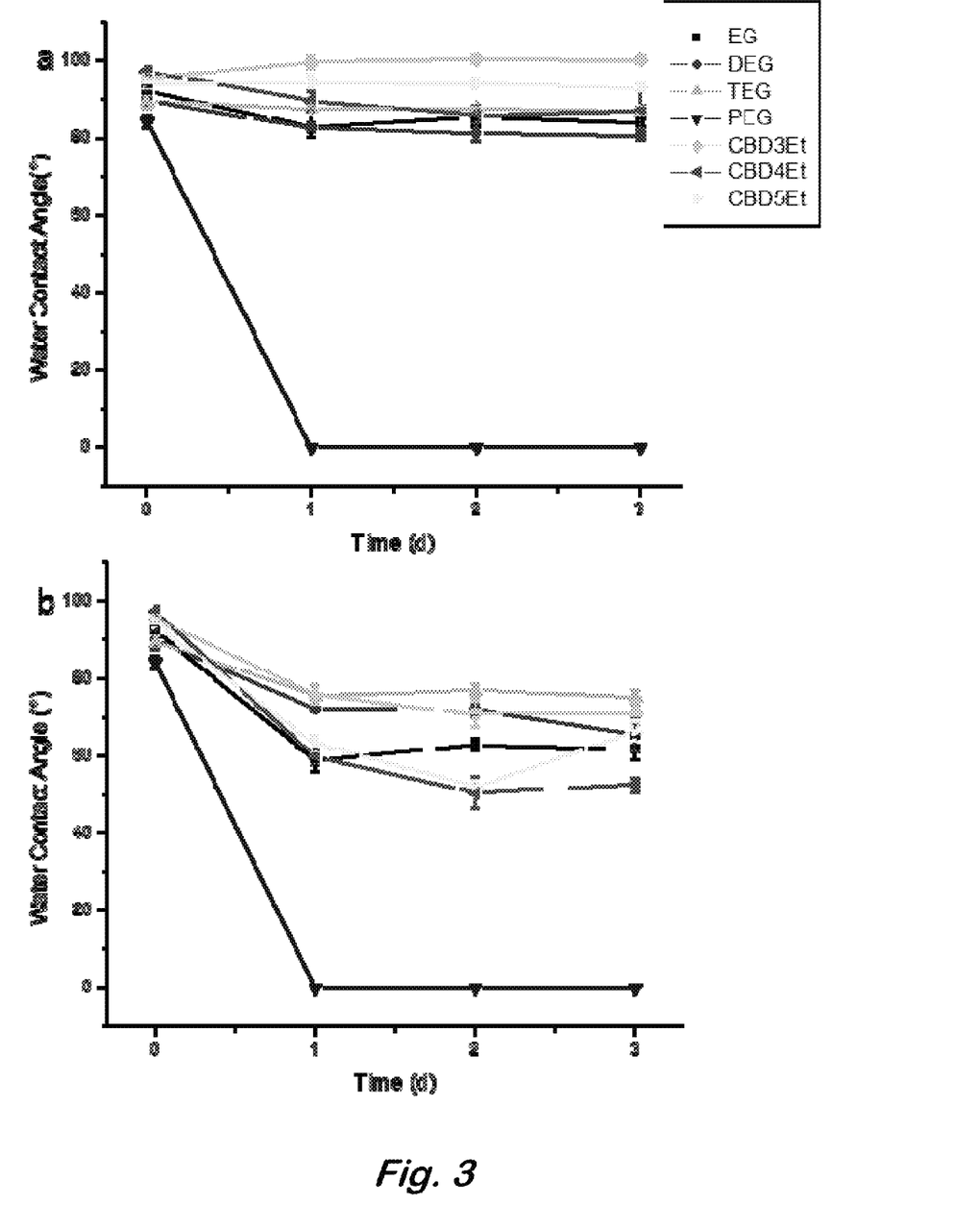
FIG. 3 shows static water contact angle of polyurethane samples after soaking in (a) water and (b) 0.5M NaOH.

Although no matrix degradation was noted and polyurethanes are traditionally characterized as being resistant to dilute alkaline conditions, both test and control samples that were exposed to aqueous NaOH did experience a general decrease in contact angle over time (FIG. 3). In numerous types of polymeric systems, alkaline conditions are commonly used to increase hydrophilicity of surfaces, however this is most often attributed to hydrolytic degradation of the polymer backbone. In this system, little if any degradation was noted over the course of 3 days soaking in 0.5 M NaOH, indicating that the cause of this depression may be a result of cooperative hydrogen bonding that is seen at high pHs compared to neat water (Tarbuck et al., "Spectroscopic Studies of Solvated Hydrogen and Hydroxide Ions at Aqueous Surfaces" *Journal of the American Chemical Society* 2006, 128 (45), 14519-14527). Specifically, hydroxide ions are able to both accept and donate hydrogen bonds with water and urethane hydrogen atoms, thereby decreasing water contact angles compared to samples soaked in neat water (Aziz et al., "Interaction between liquid water and hydroxide revealed by core-hole deexcitation" *Nature* 2008, 455 (7209), 89-91). The slight deviations between contact angle values between test and control samples after soaking in NaOH occurred as a result of the increased hydrophilicity associated with free carboxybetaine moieties post deprotection. Importantly, submersion in water for up to 3 days showed no contact angle depression for any test samples, suggesting minimal ester deprotection under neutral aqueous conditions.

Figure 4:
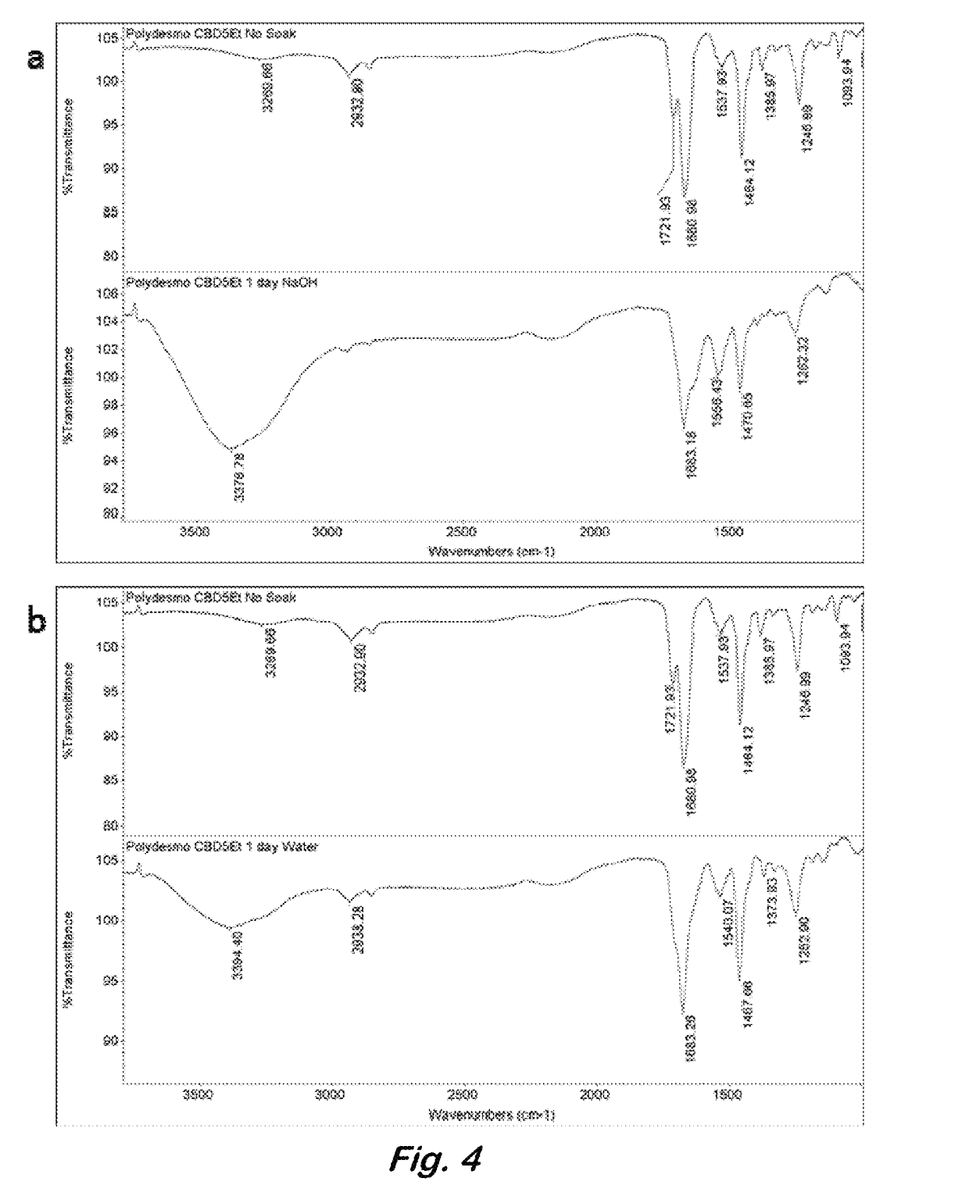
FIG. 4 shows a comparison of FTIR-ATR spectra of Polydesmo CBD5Et (a) unsoaked vs. NaOH soaked and (b) unsoaked vs. water soaked.

Surface analysis of test and control samples using FTIR-ATR indicated that exposure to aqueous NaOH did indeed result in deprotection of the ester group, while the nucleophilicity of neat water was insufficient to promote substantial hydrolysis. As can be seen in FIG. 4a, unsoaked samples of Polydesmo CBD5Et had distinct urethane and ester absorbance patterns at 1680 and 1721 $cm^{-1}$, respectively. However, upon exposure to NaOH, the ester peak largely disappeared and a shoulder at approximately 1600 $cm^{-1}$, indicative of a carboxylate anion, became evident. Furthermore, the hydroxyl stretch corresponding to water increased substantially upon exposure to the aqueous base. When soaked in water however (FIG. 4b), there was little increase in absorbance attributed to carboxylate anions and there is a slight absorbance shift of the ester peak from 1721 $cm^{-1}$ in the dry material to approximately 1700 $cm^{-1}$, indicative of hydrogen bonding of the ester group with water (Seymour et al., "Infrared Studies of Segmented Polyurethane Elastomers. I. Hydrogen Bonding" *Macromolecules* 1970, 3 (5), 579-583). Additionally, the area of the hydroxyl peak at 3400 $cm^{-1}$ was approximately 35% of that when soaked in NaOH, which correlates well with the total difference in solution uptake.

Figure 5:
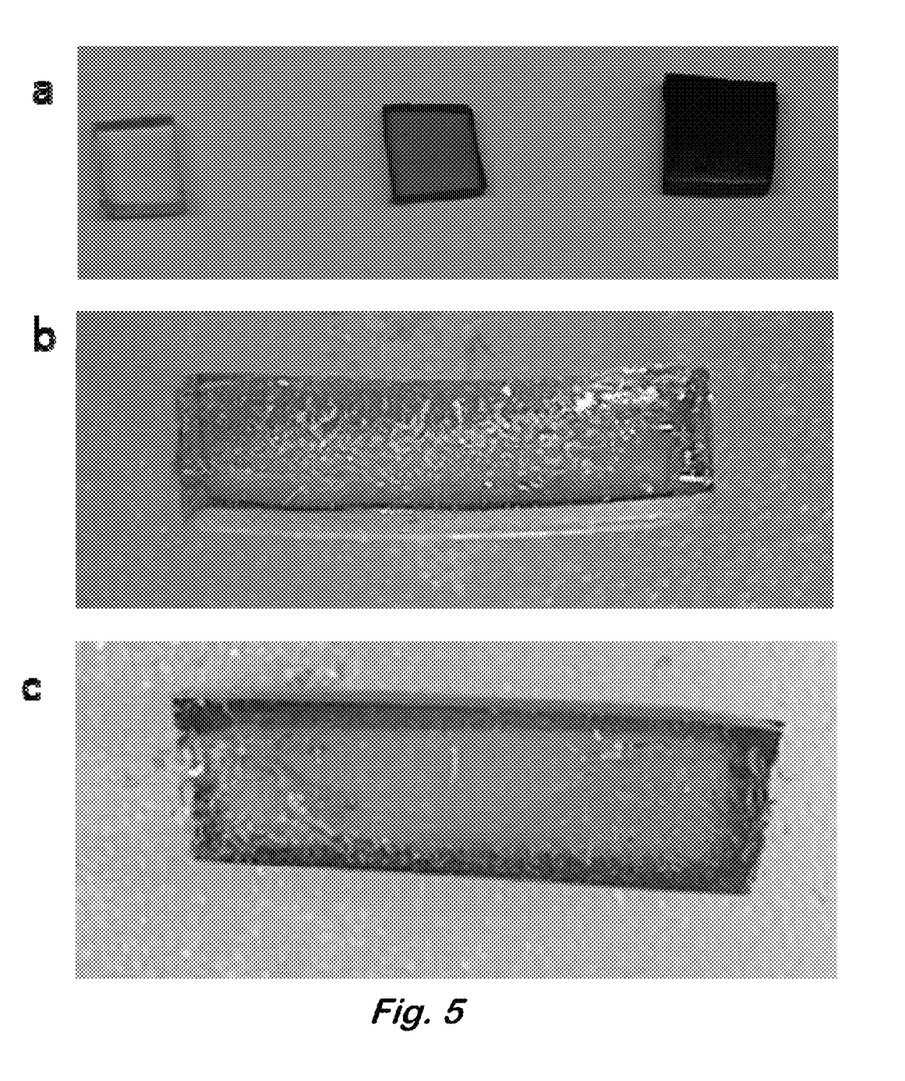
FIG. 5 shows optical images of (a) (L-R) Polydesmo EG, Polydesmo CBD3Et, and Polydesmo PEG after soaking in an aqueous methylene blue solution; (b) cross-section of untreated CBD3Et (c) cross-section of NaOH treated CBD3Et.

To qualitatively investigate the gradient deprotection mechanism, test materials were exposed to aqueous NaOH for short time periods at which point they were rinsed in water and soaked in an aqueous solution of methylene blue. The extent of water uptake in different regions of the material could then be examined visually based on the intensity of blue color. As expected, samples that exhibited low solution uptake (ex. Polydesmo EG) remained optically transparent and void of any blue color after soaking in the methylene blue solution, while those that exhibited higher degrees of water uptake exhibited optical transparency but light blue color (untreated Polydesmo CBD3Et) or opacity and dark blue color (Polydesmo PEG) depending on the extent of solution uptake (FIG. 5a). Test samples treated with NaOH behaved in the hypothesized manner with those soaked in base exhibiting a deeper blue color than those untreated, and the extent of blue color correlating with soak duration in NaOH. Importantly, when cross-sectional images were taken of Polydesmo CBD3Et without any treatment, a light blue color was observed uniformly throughout the bulk polymer (FIG. 5b). However, after a short term NaOH treatment (4 hr), a darker blue color was seen around the outermost edges of the sample, with the interior of the bulk polymer remaining a lighter blue color, similar in intensity to that of the untreated sample (FIG. 5c). This supports the hypothesis of a diffusion controlled deprotection and the preparation of a corresponding gradient hydrogel.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A polymer comprising the repeat unit:
   $X^-\{-OCH_2CH_2-N^+(CH_3)[(CH_2)_n-CO-Y]-CH_2CH_2O-CO-NH-R^2-NH-CO-\}$;
   wherein n is a positive integer;
   wherein $X^-$ is a halide;
   wherein each Y is independently selected from $O^- Z^+$ and $O-R^1$;
   wherein $Z^+$ is a cation from an aqueous base;
   wherein $R^1$ is an ester protecting group; and
   wherein $R^2$ is an organic group.
2. The polymer of claim 1, wherein n is from 1 to 5.
3. The polymer of claim 1, wherein n is 1, 3, 4, or 5.
4. The polymer of claim 1, wherein n is greater than 2.
5. The polymer of claim 1, wherein $X^-$ is $Br^-$.
6. The polymer of claim 1, wherein $Z^+$ is $Na^+$.
7. The polymer of claim 1, wherein $R^1$ is $CH_2CH_3$.
8. The polymer of claim 1, wherein $R^2$ is a residue of an aliphatic polyisocyanate.
9. The polymer of claim 1, wherein $R^2$ is a residue of hexamethylene diisocyanate or a biuret or trimer thereof.
10. A hydrogel comprising the polymer of claim 1.
11. A method comprising:
    reacting N-methyldiethanolamine with an ω-halo-n-alkanoate ester to form a compound having the formula:
    $X^-N^+(CH_3)(CH_2CH_2OH)_2[(CH_2)_n-COO-R^1]$;
    wherein n is a positive integer;
    wherein $X^-$ is a halide; and
    wherein $R^1$ is an ester protecting group; and
    reacting the compound with a polyisocyanate having the formula $OCN-R^2-NCO$ to form a polymer comprising the repeat unit:
    $X^-\{-OCH_2CH_2-N^+(CH_3)[(CH_2)_n-COO-R^1]-CH_2CH_2O-CO-NH-R^2-NH-R^2-NH-CO-\}$;
    wherein $R^2$ is an organic group.
12. The method of claim 11, wherein n is from 1 to 5.
13. The method of claim 11, wherein n is 1, 3, 4, or 5.
14. The method of claim 11, wherein n is greater than 2.
15. The method of claim 11, wherein $X^-$ is $Br^-$.
16. The method of claim 11, wherein $R^1$ is $CH_2CH_3$.
17. The method of claim 11, wherein $OCN-R^2-NCO$ is an aliphatic polyisocyanate.
18. The method of claim 11, wherein $OCN-R^2-NCO$ is hexamethylene diisocyanate or a biuret or trimer thereof.
19. The method of claim 11, further comprising:
    forming a hydrogel comprising the polymer.
20. The method of claim 11, further comprising:
    forming an article comprising the polymer; and
    exposing the article to an aqueous base that converts a portion of the $-COO-R^1$ groups to $-COO-Z^+$ groups;
    wherein $Z^+$ is the cation from the aqueous base.
21. The method of claim 20, wherein the aqueous base is NaOH.

* * * * *

UNITED STATES PATENT AND TRADEMARK OFFICE
CERTIFICATE OF CORRECTION

PATENT NO. : 9,139,684 B2
APPLICATION NO. : 13/783481
DATED : September 22, 2015
INVENTOR(S) : Peter N. Coneski et al.

It is certified that error appears in the above-identified patent and that said Letters Patent is hereby corrected as shown below:

In the Claims:

In claim number 1, column 8, line numbers 14-15, "$O^{31}Z^+$" should be "$O^-Z^+$"

In claim number 6, column 8, line number 23, "$Z^{+is\ Na+}$" should be "$Z^+$ is $Na^+$"

In claim number 11, column 8, line numbers 40-42,

"$X^-\{-OCH_2CH_2-N^+(CH_3)[(CH_2)_n-COO-R^1]-CH_2CH_2O-CO-NH-R^2-NH-R^2-NH-CO-\}$"

should be

"$X^-\{-OCH_2CH_2-N^+(CH_3)[(CH_2)_n-COO-R^1]-CH_2CH_2O-CO-NH-R^2-NH-CO-\}$"

Signed and Sealed this
Second Day of February, 2016

Michelle K. Lee
*Director of the United States Patent and Trademark Office*